(12) United States Patent
Lubkowitz et al.

(10) Patent No.: US 10,466,224 B2
(45) Date of Patent: Nov. 5, 2019

(54) METHOD AND SYSTEM FOR CONTEMPORANEOUS ANALYSIS OF A CRUDE OIL FRONT END AND A CRUDE OIL BOILING POINT DISTRIBUTION VIA A SINGLE GAS CHROMATOGRAPH

(71) Applicant: SEPARATION SYSTEMS, INC., Gulf Breeze, FL (US)

(72) Inventors: Joaquin A. Lubkowitz, Gulf Breeze, FL (US); Claudio M. Ceccarelli, Gulf Breeze, FL (US); Roberto I. Meneghini, Gulf Breeze, FL (US)

(73) Assignee: SEPARATION SYSTEMS, INC., Gulf Breeze, FL (US)

( * ) Notice: Subject to any disclaimer, the term of this patent is extended or adjusted under 35 U.S.C. 154(b) by 61 days.

(21) Appl. No.: 15/331,397

(22) Filed: Oct. 21, 2016

(65) Prior Publication Data

US 2017/0115257 A1   Apr. 27, 2017

Related U.S. Application Data

(60) Provisional application No. 62/245,127, filed on Oct. 22, 2015.

(51) Int. Cl.
| | |
|---|---|
| *G01N 30/12* | (2006.01) |
| *G01N 33/28* | (2006.01) |
| *G01N 30/24* | (2006.01) |
| *G01N 30/88* | (2006.01) |
| *G01N 30/46* | (2006.01) |

(Continued)

(52) U.S. Cl.
CPC ......... *G01N 33/2823* (2013.01); *G01N 30/24* (2013.01); *G01N 30/88* (2013.01); *G01N 30/466* (2013.01); *G01N 30/54* (2013.01); *G01N 2030/3007* (2013.01); *G01N 2030/8854* (2013.01)

(58) Field of Classification Search
None
See application file for complete search history.

(56) References Cited

U.S. PATENT DOCUMENTS

| | | | |
|---|---|---|---|
| 4,869,876 A * | 9/1989 | Arfman | G01N 30/30 422/89 |
| 5,116,764 A | 5/1992 | Annino et al. | |

(Continued)

FOREIGN PATENT DOCUMENTS

| | | |
|---|---|---|
| WO | 2010101453 A2 | 9/2010 |
| WO | 2010116389 A1 | 10/2010 |

OTHER PUBLICATIONS

International Search Report and Written Opinion of related International Patent Application No. PCT/US2016/058438 dated Jan. 3, 2017.

*Primary Examiner* — Paul M. West
*Assistant Examiner* — Mark A Shabman
(74) *Attorney, Agent, or Firm* — Arent Fox LLP

(57) ABSTRACT

A gas chromatography instrument comprising a first autoinjector in communication with a first column, a second autoinjector in communication with a second column, a first flame ionization detector in communication with the first column, a second flame ionization detector in communication with the second column, wherein the first column is housed in a first compartment and the second column is housed in a second compartment.

15 Claims, 2 Drawing Sheets

(51) Int. Cl.
  *G01N 30/54*  (2006.01)
  *G01N 30/30*  (2006.01)

(56) References Cited

U.S. PATENT DOCUMENTS

| | | | | |
|---|---|---|---|---|
| 5,699,269 A | * | 12/1997 | Ashe | G01N 33/2823 |
| | | | | 436/29 |
| 6,530,260 B1 | * | 3/2003 | Mustacich | G01N 30/30 |
| | | | | 210/198.2 |
| 6,711,532 B1 | | 3/2004 | Spieksma | |
| 7,387,811 B2 | * | 6/2008 | Selvamanickam | C23C 16/408 |
| | | | | 29/599 |
| 8,303,694 B2 | * | 11/2012 | Tipler | G01N 30/20 |
| | | | | 73/23.35 |
| 8,621,912 B2 | | 1/2014 | Guieze | |
| 2007/0050154 A1 | * | 3/2007 | Albahri | G01N 25/14 |
| | | | | 702/22 |
| 2008/0105032 A1 | | 5/2008 | Reddy et al. | |
| 2013/0236276 A1 | * | 9/2013 | Richter | B01L 3/00 |
| | | | | 414/222.07 |
| 2013/0276512 A1 | * | 10/2013 | Bae | G01N 30/02 |
| | | | | 73/23.35 |

* cited by examiner

METHOD AND SYSTEM FOR CONTEMPORANEOUS ANALYSIS OF A CRUDE OIL FRONT END AND A CRUDE OIL BOILING POINT DISTRIBUTION VIA A SINGLE GAS CHROMATOGRAPH

CROSS-REFERENCE TO RELATED APPLICATIONS

This application claims the benefit of U.S. Provisional Patent Application No. 62/245,127, entitled "Method and System for Contemporaneous Analysis of a Crude Oil Front End and a Crude Oil Boiling Point Distribution via a Single Gas Chromatograph," filed on Oct. 22, 2015, which is expressly incorporated by reference herein in its entirety.

BACKGROUND

Gas Chromatography is a means of chemical analysis used for separating chemicals in a complex sample. A gas chromatograph uses a narrow tube, known as a column, through which different chemical constituents of a sample pass in a gas stream. The gas stream is also called the carrier gas or mobile phase. Gas Liquid Chromatography (GLC), or simply Gas Chromatography (GC), is a type of chromatography in which the mobile phase is a gas. The mobile phase (i.e., a gas stream) is passed through a column with a phase coating, which is called the stationary phase and which is a microscopic layer of liquid on an inert solid wall of the column. The column is often flexible so that a very long column can be wound into a small coil. As the chemical constituents exit the end of the column, they are detected and identified electronically.

In GC, the chemical constituents within a sample pass through the column at different rates, depending on their various chemical and physical properties and their interaction with a specific column filling. Chemical constituents are characterized by the different rates by which they flow through, or elute from, the column. This rate corresponds with the constituents' individual retention time (i.e., the length of time between the injection of the sample and the detection of the individual component). In many cases, constituents with different boiling points have different retention times. Other parameters can also be used to alter the order or retention time, such as the carrier gas flow rate.

The column(s) in a GC are contained in an oven, the temperature of which is precisely controlled (e.g., electronically). The rate at which a sample passes through the column is directly proportional to the temperature of the column.

One application of GC is for the analysis of crude oil. Crude oil, for example, may contain a mixture of chemical compounds from a family of several hundred chemical compounds. Some chemicals that may be found in crude oil include hexane, jet fuels, mineral oils, benzene, toluene, xylenes, naphthalene, and fluorine, in addition to other petroleum products and gasoline components.

One useful tool for analyzing crude oil is its boiling point (BP) curve, as boiling point range is often a key controlling parameter for manufacturing petroleum products. GC is routinely employed for determining the boiling point range of oil products, as it is a fast and inexpensive method for providing information regarding the fuel-type present. A BP curve is a quantitative percent mass yield as a function of the boiling point of the hydrocarbon components of a sample.

However, in the case of crude oil, two column systems are often required since the crude oil BP curve obtained by high temperature columns is not accurate in the region of Initial Boiling Point up to 25% of the BP curve, generally comprising methane through nonane. As a result, a second injection is conventionally made in a separate instrument to analyze the crude oil fraction in the region of methane through nonane. This second injection is often analyzed and identified using a Detailed Hydrocarbon Analysis (DHA) column. The identification on this longer DHA column is often used for providing the boiling point in the region up to 25%. In many cases, the DHA column requires different temperatures than the high temperature columns, thereby preventing both columns from being housed in a single gas chromatograph oven. Generally DHA columns are designed such that they have a limited temperature range and cannot coexist in the same oven as a crude oil column, which is heated to high temperatures.

SUMMARY AND DETAILED DESCRIPTION

The present invention provides a gas chromatography instrument comprising: a first autoinjector in communication with a first column and a second autoinjector in communication with a second column, and a first flame ionization detector in communication with the first column and a second flame ionization detector in communication with the second column, wherein the first column is housed in a first compartment and the second column is housed in a second compartment.

Aspects of the present invention relate to Gas Chromatography (GC) systems and methods, which provide for more efficiently determining the composition of crude oils and fractions thereof. Systems and methods in accordance with aspects of the present invention advantageously avoid the use of two separate instruments, which have previously been required due to different operational temperatures of the columns utilized in GC crude oil analysis, for example. Systems and methods in accordance with aspects of the present invention allow the characterization of a crude oil in one single instrument by the contemporaneous injection of a crude oil sample into two columns, thereby saving both time and expense.

Figure 1:
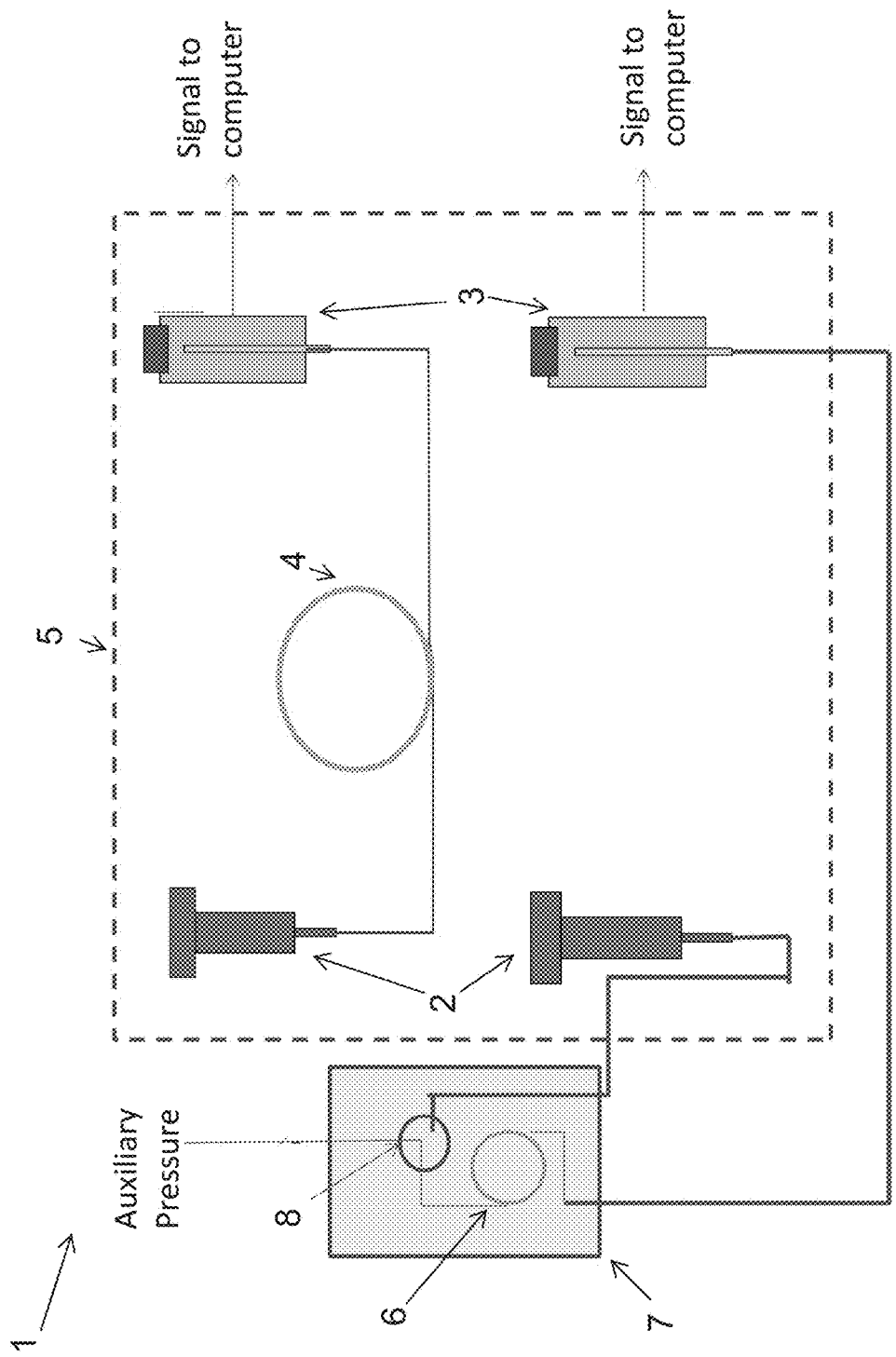
FIG. 1 shows an example of a GC system in accordance with aspects of the present invention.

An example of a GC system according to aspects of the present invention is shown in FIG. 1. According to aspects of the present invention, the system may comprise a single GC instrument (1), wherein the instrument includes two autoinjectors (2), a first column and a second column, one temperature programmable inlet, a split splitless inlet, and two flame ionization detectors (3).

According to some variations, aspects of the present invention may include a GC instrument comprising or consisting of two capillary columns, each column being housed in a separate space or compartment in the GC instrument. For example, as shown in FIG. 1, one capillary column (4) may be housed in a main GC oven (5), while a second capillary column (6) may be housed in a separate compartment (7) other than the main GC oven. According to aspects of the present invention, the separate compartment (7) may be configured to thermally house the second column (6), e.g., a DHA column. For example, the separate compartment may be an insulated thermal housing which is configured to isolate the second column (6), e.g., a DHA column, from other compartments of the GC instrument and/or the environment.

According to aspects of the present invention, the second column (6), e.g., a DHA column, may be heated. For example, the DHA column may be heated by electronics in the GC instrument, such as electronics that are already present in the GC instrument to control heat for the first column, thereby not requiring specific and/or additional heating electronics. That is, an electronic device that provides heat to the second column may also provide heat to at least one other component of the instrument. In some embodiments, the DHA column may be encased by or wrapped with a thin film heater. According to aspects of the present invention, the DHA column may be uniformly heated with a heater. For example, the heater may comprise a wire in a thin film. According to some aspects, the heater may be configured to be compatible with the wattage produced by electronics in the GC instrument. The heater, such as the thin film heater, may, for example, be covered with aluminum foil or other similarly performing material.

According to some aspects of the present invention, the heated DHA column surprisingly provides repeatable retention times through analysis times up to about 90 minutes of the order of about 0.01 min.

According to aspects of the present invention, the instruments may be provided with features for controlling and/or limiting the temperature of one or both capillary columns, wherein the features may comprise, for example, a controller. For example, the temperature of the DHA column may be controlled by the controller and/or other features so as to not rise above about 300° C. (i.e., to a maximum of about 300° C.). In some embodiments, the DHA column may be temperature sensitive. According to some aspects, the temperature of the first capillary column may be controlled so as to reach a temperature necessary for the boiling point determination of a sample, such as a crude oil sample. For example, the temperature of the first capillary column may be controlled so as to reach a temperature of at least 430° C.

According to aspects of the present invention, as shown in FIG. 1, the compartment (7) that houses the second column (6), e.g., a DHA column, may comprise a liquid coolant distributor. The liquid coolant distributor may comprise a liquid coolant valve and a shower head configured to distribute coolant uniformly. In some embodiments, the shower head may comprise a circular shower head portion. According to some aspects, the shower head may be configured such that a liquid, e.g., liquid coolant, distributed therethrough is distributed through two or more orifices. According to some aspects, the shower head is configured such that a liquid, e.g., liquid coolant, is distributed through multiple orifices in the shower head. The liquid coolant valve and the shower head together may be configured to allow rapid cooling at the end of a heating cycle and/or operation at sub-ambient temperatures, for example.

According to aspects of the present invention, the compartment that houses the DHA column may also house a microfluidic switch (8). In some embodiments, the microfluidic switch (8) may be configured to allow a preselected fraction of a sample to enter the DHA column. According to some embodiments, the microfluidic switch may also be heated. The microfluidic switch (8) may be, for example, heated independently from either capillary column.

According to aspects of the present invention, the system may also be configured to utilize one or more separate computer systems. For example, certain embodiments include two separate computer systems (i.e., a first computer system and a second computer system) wherein the first computer system may be used to provide the boiling point curve of a crude oil sample obtained in a first capillary column (4), and the second computer system may be used to identify components, such as those from methane through nonane, obtained in the second column (6). In some embodiments, the instrument may comprise another separate computer system (e.g., a third computer system) capable of merging the two BP curves, thereby rendering a final, accurate BP curve. In some embodiments, the computer system capable of merging the two BP curves may be comprised within the same system used to identify components (i.e., the second computer system), such as those from methane through nonane, obtained in the DHA column.

Figure 2:
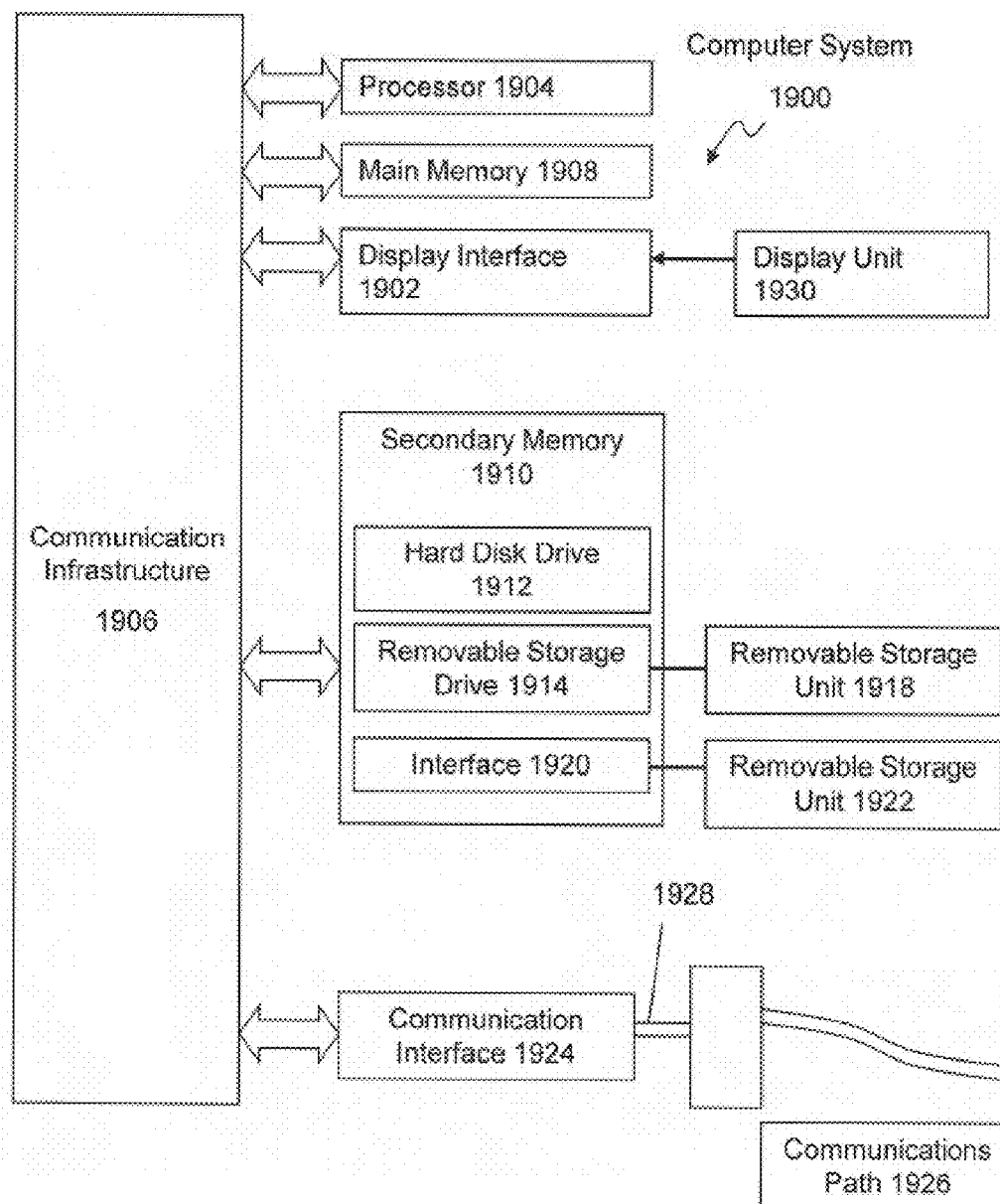
FIG. 2 shows an example computer system for use in accordance with aspects of the present invention.

Aspects of the invention may be implemented using hardware, software or a combination thereof and may be implemented in one or more computer systems or other processing systems. In one variation, aspects of the invention are directed toward one or more computer systems capable of carrying out the functionality described herein. An example of such a computer system 1900 is shown in FIG. 2.

Computer system 1900 includes one or more processors, such as processor 1904. The processor 1904 is connected to a communication infrastructure 1906 (e.g., a communications bus, cross-over bar, or network). Various software aspects are described in terms of this exemplary computer system. After reading this description, it will become apparent to a person skilled in the relevant art(s) how to implement the aspects of invention using other computer systems and/or architectures.

Computer system 1900 can include a display interface 1902 that forwards graphics, text, and other data from the communication infrastructure 1906 (or from a frame buffer not shown) for display on the display unit 1930. Computer system 1900 also includes a main memory 1908, preferably random access memory (RAM), and may also include a secondary memory 1910. The secondary memory 1910 may include, for example, a hard disk drive 1912 and/or a removable storage drive 1914, representing a floppy disk drive, a magnetic tape drive, an optical disk drive, etc. The removable storage drive 1914 reads from and/or writes to a removable storage unit 1918 in a well-known manner. Removable storage unit 1918, represents a floppy disk, magnetic tape, optical disk, etc., which is read by and written to removable storage drive 1914. As will be appreciated, the removable storage unit 2018 includes a computer usable storage medium having stored therein computer software and/or data.

In alternative variations, secondary memory 1910 may include other similar devices for allowing computer programs or other instructions to be loaded into computer system 1900. Such devices may include, for example, a removable storage unit 1922 and an interface 2920. Examples of such may include a program cartridge and cartridge interface (such as that found in video game devices), a removable memory chip (such as an erasable programmable read only memory (EPROM), or programmable read only memory (PROM)) and associated socket, and other removable storage units 1922 and interfaces 1920, which allow software and data to be transferred from the removable storage unit 1922 to computer system 1900.

Computer system 1900 may also include a communications interface 1924. Communications interface 1924 allows software and data to be transferred between computer system 1900 and external devices. Examples of communications interface 1924 may include a modem, a network interface (such as an Ethernet card), a communications port, a Personal Computer Memory Card International Association (PCMCIA) slot and card, etc. Software and data transferred via communications interface 1924 are in the form of signals 1928, which may be electronic, electromagnetic, optical or other signals capable of being received by communications interface 1924. These signals 1928 are provided to communications interface 1924 via a communications path (e.g., channel) 1926. This path 1926 carries signals 1928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 1914, a hard disk installed in hard disk drive 1912, and signals 1928. These computer program products provide software to the computer system 1900. Aspects of the invention are directed to such computer program products.

Computer programs (also referred to as computer control logic) are stored in main memory 1908 and/or secondary memory 1910. Computer programs may also be received via communications interface 2024. Such computer programs, when executed, enable the computer system 1900 to perform the features in accordance with aspects of the invention, as discussed herein. In particular, the computer programs, when executed, enable the processor 1904 to perform such features. Accordingly, such computer programs represent controllers of the computer system 1900.

In a variation where aspects of the invention are implemented using software, the software may be stored in a computer program product and loaded into computer system 1900 using removable storage drive 1914, hard drive 1912, or communications interface 1924. The control logic (software), when executed by the processor 1904, causes the processor 1904 to perform the functions as described herein. In another variation, aspects of the invention are implemented primarily in hardware using, for example, hardware components, such as application specific integrated circuits (ASICs). Implementation of the hardware state machine so as to perform the functions described herein will be apparent to persons skilled in the relevant art(s).

In yet another variation, aspects of the invention are implemented using a combination of both hardware and software.

While aspects of this invention have been described in conjunction with the example features outlined above, alternatives, modifications, variations, improvements, and/or substantial equivalents, whether known or that are or may be presently unforeseen, may become apparent to those having ordinary skill in the art. Accordingly, the example aspects of the invention, as set forth above, are intended to be illustrative, not limiting. Various changes may be made without departing from the spirit thereof. Therefore, aspects of the invention are intended to embrace all known or later-developed alternatives, modifications, variations, improvements, and/or substantial equivalents.

What is claimed is:

1. A gas chromatography instrument comprising:
   a first autoinjector in communication with a first column and a second autoinjector in communication with a second column,
   a first flame ionization detector in communication with the first column and a second flame ionization detector in communication with the second column,
   a first computer system,
   a second computer system, and
   a third computer system,
   wherein the first column is housed in a first compartment and the second column is housed in a second compartment,
   wherein the first compartment comprises a GC oven,
   wherein the second compartment comprises a microfluidic switch and an insulated thermal housing configured to isolate the second column,
   wherein the first computer system utilizes data obtained from the first column to provide a boiling point curve of a sample being analyzed in the first column,
   wherein the second computer system utilizes data obtained from the second column to identify a component of a sample being analyzing in the second column, and
   wherein the third computer system utilizes data from both the first computer system and the second computer system.

2. The gas chromatography instrument of claim 1, wherein the second column is a Detailed Hydrocarbon Analysis (DHA) column.

3. The gas chromatography instrument of claim 1, further comprising a heater configured to heat the second column.

4. The gas chromatography instrument of claim 3, wherein the heater is a thin film heater.

5. The gas chromatography instrument of claim 3, wherein the heater heats the second column to a maximum of 300° C.

6. The gas chromatography instrument of claim 1, wherein an electronic device that provides heat to the second column also provides heat to at least one other component of the instrument.

7. The gas chromatography instrument of claim 1, further comprising a first controller that controls the temperature of the first column.

8. The gas chromatography instrument of claim 7, wherein the first controller is configured such that the temperature of the first column is at least a temperature necessary to determine a boiling point of a sample being analyzed in the first column.

9. The gas chromatography instrument of claim 8, wherein the sample is crude oil.

10. The gas chromatography instrument of claim 1, wherein the second compartment comprises a liquid coolant distributor.

11. The gas chromatography instrument of claim 10, wherein the liquid coolant distributor comprises a valve and a shower head.

12. The gas chromatography instrument of claim 1, wherein the microfluidic switch is configured to provide a preselected fraction of a sample to the second column.

13. The gas chromatography instrument of claim 12, further comprising a heating mechanism configured to heat the microfluidic switch.

14. The gas chromatography instrument of claim 1, wherein the first column is a capillary column configured for use at a temperature required to determine a boiling point of a crude oil sample.

15. The gas chromatography instrument of claim 1, further comprising a heating electronic system, wherein a temperature of the first column and a temperature of the second column are controlled by the heating electronic system.

* * * * *